(12) United States Patent
Choi et al.

(10) Patent No.: US 9,555,240 B2
(45) Date of Patent: Jan. 31, 2017

(54) SYSTEM AND METHOD FOR SKELETAL MUSCLE STIMULATION

(71) Applicant: Samsung Electronics Co., Ltd., Suwon-si (KR)

(72) Inventors: Chang Mok Choi, Seoul (KR); Byung Hoon Ko, Hwaseong-si (KR); Kun Soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 131 days.

(21) Appl. No.: 14/058,407

(22) Filed: Oct. 21, 2013

(65) Prior Publication Data

US 2014/0188188 A1    Jul. 3, 2014

(30) Foreign Application Priority Data

Dec. 28, 2012  (KR) .................. 10-2012-0156356

(51) Int. Cl.
| | | |
|---|---|---|
| A61N 1/36 | (2006.01) | |
| A61B 5/0488 | (2006.01) | |
| A61N 1/372 | (2006.01) | |
| A61N 1/04 | (2006.01) | |
| A61B 5/00 | (2006.01) | |

(52) U.S. Cl.
CPC ......... *A61N 1/36003* (2013.01); *A61B 5/0488* (2013.01); *A61B 5/4836* (2013.01); *A61N 1/0452* (2013.01); *A61N 1/37247* (2013.01); *A61N 1/37258* (2013.01); *A61N 1/37282* (2013.01); *A61B 5/002* (2013.01)

(58) Field of Classification Search
CPC ............ A61N 1/36003; A61N 1/37247; A61N 1/37258; A61N 1/0452; A61N 1/37282; A61B 5/4836; A61B 5/0488; A61B 5/002
See application file for complete search history.

(56) References Cited

U.S. PATENT DOCUMENTS

| | | | | |
|---|---|---|---|---|
| 8,412,338 B2 * | 4/2013 | Faltys | .............................. | 607/50 |
| 2009/0171417 A1 * | 7/2009 | Philipson | ......................... | 607/48 |

FOREIGN PATENT DOCUMENTS

| | | |
|---|---|---|
| JP | 2005-013372 A | 1/2005 |
| JP | 2011-245014 A | 12/2011 |
| KR | 10-2005-0033923 A | 4/2005 |
| KR | 10-0550673 B1 | 2/2006 |
| KR | 10-0602844 B1 | 7/2006 |
| KR | 10-1155233 B1 | 6/2012 |

OTHER PUBLICATIONS

Lyons, G. M., et al. "An investigation of the effect of electrode size and electrode location on comfort during stimulation of the gastrocnemius muscle." *Medical engineering & physics* 26.10 (2004): 873-878.

\* cited by examiner

*Primary Examiner* — Rex R Holmes
(74) *Attorney, Agent, or Firm* — NSIP Law

(57) ABSTRACT

A system and method for skeletal muscle stimulation is provided for increasing muscle mass by stimulating a muscle in an optimal condition through a stimulus signal from an electrical stimulation device disposed at a stimulation position.

8 Claims, 6 Drawing Sheets

SYSTEM AND METHOD FOR SKELETAL MUSCLE STIMULATION

CROSS-REFERENCE TO RELATED APPLICATION

This application claims the benefit under 35 U.S.C. §119(a) of Korean Patent Application No. 10-2012-0156356, filed on Dec. 28, 2012, in the Korean Intellectual Property Office, the entire disclosure of which is incorporated herein by reference for all purposes.

BACKGROUND

1. Field

The following description relates to a system and method for skeletal muscle stimulation.

2. Description of Related Art

Sarcopenia is the degenerative loss of muscle mass due to aging. This disease is commonly seen in the elderly, and about 40% of people over the age of 65 are afflicted by this disease. When muscle mass is reduced by sarcopenia or other muscle degenerative diseases, basal metabolism typically decreases. A person with decreased basal metabolism typically gains weight easily and becomes susceptible to chronic diseases such as hypertension, and the like. When a muscle of the lower body is weakened by a loss of muscle mass, an everyday activity such as walking may be made difficult, and a person typically becomes more vulnerable to injuries related to the weakened muscular abilities. For example, injuries related to falling while walking may become more frequent.

A muscle has a combination of slow twitch muscle fibers and fast twitch muscle fibers. Slow twitch muscle fibers are characterized by high endurance and slow contraction speeds. For example, slow twitch muscle fibers are typically more common in muscles of marathon athletes. Fast twitch muscle fibers have faster contraction speeds and are typically used during high agility exercises. For example, fast twitch muscle fibers are used for everyday activities such as lifting an object. Activities such as lifting an object typically require an application of an instant high intensity force. Dynamic activities of the slow twitch muscle fibers and the fast twitch muscle fibers are most frequently found in people in their twenties.

However, as humans age, the slow twitch muscle fibers and the fast twitch muscle fibers gradually start to degenerate. Slow twitch muscle fibers exhibit a gradual atrophy whereas atrophy of fast twitch muscle fibers is much less gradual. For example, slow twitch muscle fibers may be maintained in people having seventy years of age in order to facilitate walking for long periods of time. On the other hand, statistics have found that all fast twitch muscle fibers may degenerate at once when humans enter their thirties.

One way of suppressing atrophy of fast twitch muscle fibers and reduction in muscle mass is through routine and frequent exercise. However, studies have shown that finding sufficient time for routine exercise is difficult. Accordingly, routine exercise is typically not a feasible model for suppressing muscle atrophy.

SUMMARY

In a general aspect, there is provided an apparatus for muscle stimulation, the apparatus including an electrical stimulation device configured to output a stimulus signal to a stimulation position based on an electromyogram (EMG) signal.

The electrical stimulation device may be further configured to output the stimulus signal in response to the EMG signal satisfying a tolerance.

The electrical stimulation device may be wireless, the stimulus signal may be output via an electrode, and the EMG signal may be measured using the electrode.

The electrical stimulation device may be configured to determine that the EMG signal satisfies the tolerance in response to a distribution of the EMG signal being greater than or equal to a reference distribution value for a muscle in a contracted state.

The electrical stimulation device may be configured to determine that the EMG signal fails to satisfy the tolerance, and outputs information for adjusting a position at which the electrode is attached, in response to a distribution of the EMG signal being less than a reference distribution value for a muscle in a contracted state.

The electrical stimulation device may include a power supply configured to generate the stimulus signal; and a differential amplifier configured to measure the EMG signal.

The apparatus may further include a terminal configured to output guide information to enable a user to attach the electrode to the stimulation position in response to an input from the user.

The guide information may include an image or an illustration.

The guide information may corresponds to a muscle that is identified is response to the input from the user.

The terminal device may be configured to provide a pattern of applying the stimulus signal for contracting or relaxing the muscle.

In another general aspect, there is provided a terminal for muscle stimulation, including a display configured to output information to guide attaching an electrode to a stimulation position, wherein the terminal is configured to enable editing of a pattern of a stimulus signal.

The display is further configured to output the information in response to an input from the user; the stimulus signal may be output via the electrode; and the terminal may be further configured to enable the user to edit the pattern of the stimulus signal through a selection from the user.

In another general aspect, there is provided a method for muscle stimulation including receiving an input from a user relating to a stimulation position; and outputting guide information representing a location of the stimulation position in response to the input from the user.

The location of the stimulation position may represent a location at which an electrode is attached for muscle stimulation.

The method may include receiving another input from the user with respect to a pattern of a stimulus signal; and providing information about the pattern of the stimulus signal as edited by the user in response to the another input.

The method may further include determining whether an EMG signal, measured using an electrode attached at the stimulation position, satisfies a tolerance.

The method may further include outputting a stimulus signal to the stimulation position via the electrode when the EMG signal satisfies the tolerance.

The method may further include determining that the EMG signal satisfies the tolerance in response to a distribution of the EMG signal being greater than or equal to a reference distribution value for a muscle in a contracted state.

The method may further include determining that the EMG signal fails to satisfy the tolerance, and outputting information for adjusting a position of the electrode, in response to a distribution of the EMG signal being less than a reference distribution value for a muscle in a contracted state.

DETAILED DESCRIPTION

Figure 1:
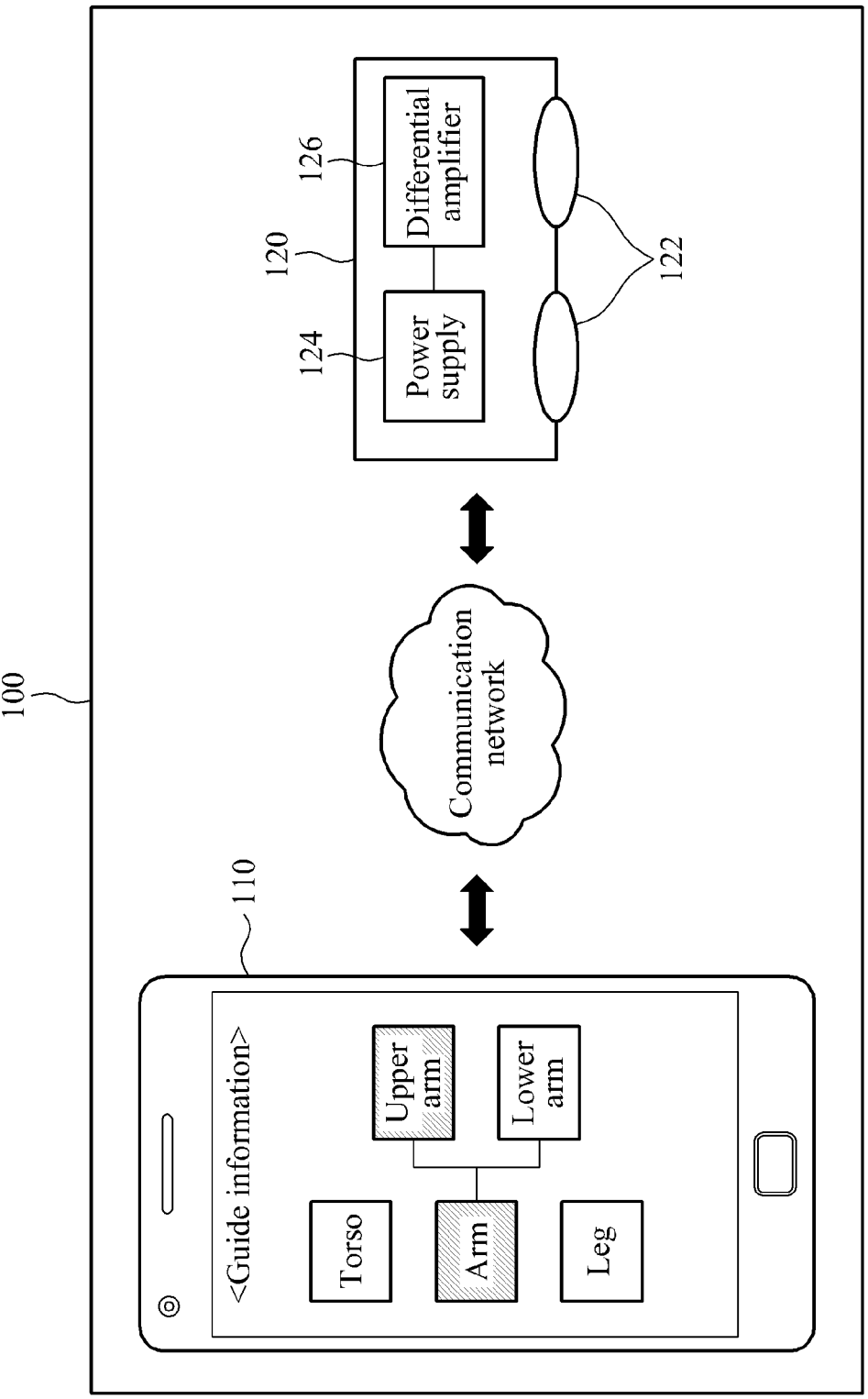
FIG. 1 is a diagram illustrating an example of a system for skeletal muscle stimulation.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

As described throughout, an electrode may be to a predetermined portion of a user's body. The position in which the electrode is attached is hereinafter referred to as a stimulation position. In this example, the electrode is used to strengthen a muscle and send a stimulus signal from an external power supply to the stimulation position. For example, the electrode stimulates the stimulation position by outputting the stimulus signal generated based on a predetermined pattern in an electrical stimulation device.

In this example, the electrode is connected to a differential amplifier for determining the precise location of the stimulation position and detecting an electromyogram (EMG) signal generated in the user's body.

The electrical stimulation device may refer to a means for outputting a stimulus signal generated based on a pattern received wirelessly from a terminal device via the electrode. Thus, in this example, the electrical stimulation device includes a power supply for generating the stimulus signal.

In an example, the electrical stimulation device measures the EMG signal at a current position to determine whether the electrode is disposed precisely at the predetermined stimulation position. In response to determining whether the position is precise, the stimulus signal may be generate. The signal stimulation device may output the stimulus signal in response to determining that the electrode is disposed at the precise stimulation position. In this example, the electrical stimulation device determines that the electrode is disposed precisely at the predetermined stimulation position when a distribution value of the EMG signal is measured to be within a predetermined tolerance.

In an example, a terminal device generates an optimal pattern for stimulating the stimulation position or an associated region and transmits the optimal pattern to the electrical stimulation device. The terminal device outputs guide information such that the selection of the stimulation position and stimulation pattern may be possible by user selection.

A wireless system for skeletal muscle stimulation enables a user to dispose the electrical stimulation device at a precise stimulation position with ease and without anatomical knowledge of the body.

In this example, the wireless system for skeletal muscle stimulation increases muscle mass by stimulating the muscle under an optimal condition via a stimulus signal from the electrical stimulation device disposed precisely at a predetermined stimulation position.

FIG. 1 illustrates an example of a system 100 for skeletal muscle stimulation.

Referring to FIG. 1, the system 100 includes a terminal device 110 and an electrical stimulation device 120.

In this example, the terminal device 110 outputs guide information to induce a stimulation position to be predetermined. The guide information includes a hierarchically classified menu to allow a user to readily determine or select a stimulation position.

For example, the terminal device 110 provides a user with the option of "torso/arm/leg" in a main item field of the menu. If "arm" is selected, menu selections of "upper arm/lower arm" in a sub-item field allow further selection by the user. When "upper arm" is selected by the user, the terminal device 110 determines a portion of a muscle belonging to the "upper arm" to be stimulated. This portion is disposed to be the stimulation position.

Once the stimulation position is determined, the terminal device 110 provides information about the stimulation position. For example, the terminal device 110 may provide information relating to the location of the stimulation position in the body, a shape of an associated muscle, usage of the muscle, and the like. The terminal device 110 allows the user to easily perceive the stimulation position by visually displaying this information in a graphical form. In an example, once "upper arm" is selected, the terminal device 110 directs the user of the location of the stimulation position by visually displaying graphical information associated with a muscle belonging to the upper arm. Further, text information is provided reading "a stimulation position is a location identified by lifting of a thumb."

The terminal device 110 generates a pattern that stimulates the stimulation position optimally and transmits the pattern wirelessly. A communication network is used to transmit information, such as the pattern of stimulation, from the terminal device 110 to the electrical stimulation device 120 disposed at the stimulation position. In an example, the pattern is a type of program for strengthening a muscle by repeated periods of muscle relaxation and contraction. For example, the program includes creating a cycle of relaxation and contraction periods by applying a stimulus signal to the muscle. The pattern may include a combination of original or repeated stimulation periods and non-stimulation periods by outputting or not outputting a stimulus signal, respectively. The patter may be based on a plurality of different features of the muscle being stimulated.

In an example, the terminal device 110 generates the pattern by programming information prescribed by an expert such as a doctor or medical professional. In another example, the pattern is programmed by the user directly within an allowed range that is medically harmless to the body.

The electrical stimulation device 120 generates a stimulus signal based on the pattern and outputs the stimulus signal to the stimulation position via an electrode 122. The pattern is input wirelessly through a communication network from the terminal device 110 to the electrical stimulation device 120. In this example, the electrical stimulation device 120 includes a power supply 124 for generating the stimulus signal based on an electrical signal emitted from the power supply 124.

In an example where a brachialis muscle belonging to an upper arm is predetermined as the stimulation position by the wireless terminal device 110, the electrical stimulation device 120 may generate a stimulus signal based on a pattern. For example, the electrical stimulation device 120 may generate a stimulus signal for one minute via the electrode 122, suspend the generating of the stimulus signal for thirty seconds, and repeat the one minute stimulation and thirty second pause stimulation pattern for a period of 20 minutes.

In an example, the electrical stimulation device 120 determines whether a portion with which the body is in contact with the electrode 122 coincides with the predetermined stimulation position. In this example, the electrical stimulation device 120 includes a differential amplifier 126 for measuring an EMG signal occurring at a location with which the body is currently in contact with the electrode 122. A distribution of the EMG signal calculated by the differential amplifier 126 is compared with a predetermined reference distribution value. A detecting of the EMG signal may be performed in the electrode 122 with which the body is in contact.

For example, when a muscle is in a contracted state, the electrical stimulation device 120 determines electrode 122 is disposed precisely at the predetermined stimulation position. When the distribution of the EMG signal is greater than or equal to a predetermined reference distribution value then the EMG signal satisfies a predetermined tolerance and the electrode 122 is determined to be disposed at the stimulation position.

Further to this example, when a muscle is in a contracted state, the electrical stimulation device 120 determines when the electrode 122 is not precisely placed at the predetermined stimulation position. When the distribution of the EMG signal is less than the predetermined reference distribution value then the EMG signal fails to satisfy the predetermined tolerance and the electrode is determined to be placed imprecisely. In this example, the electrical stimulation device 120 outputs information for adjusting a position of the electrode 122. For example, a positioning information message, a warning alarm, and the like, are output for directing a user to move the position of the electrode 122.

Accordingly, the system 100 for skeletal muscle stimulation may allow the precise placement of the electrical stimulation device 120 at a predetermined stimulation position by providing a user with guide information in the terminal device 110 and measuring the EMG signal in the electrical stimulation device 120. Thus, the system 100 does not necessarily refer to specific anatomical information for directing a user on placement of the device 120.

By outputting a stimulus signal to stimulate the muscle of the stimulation position based on a pattern, muscle atrophy of the elderly can be prevented without physical exercise.

Figure 2:
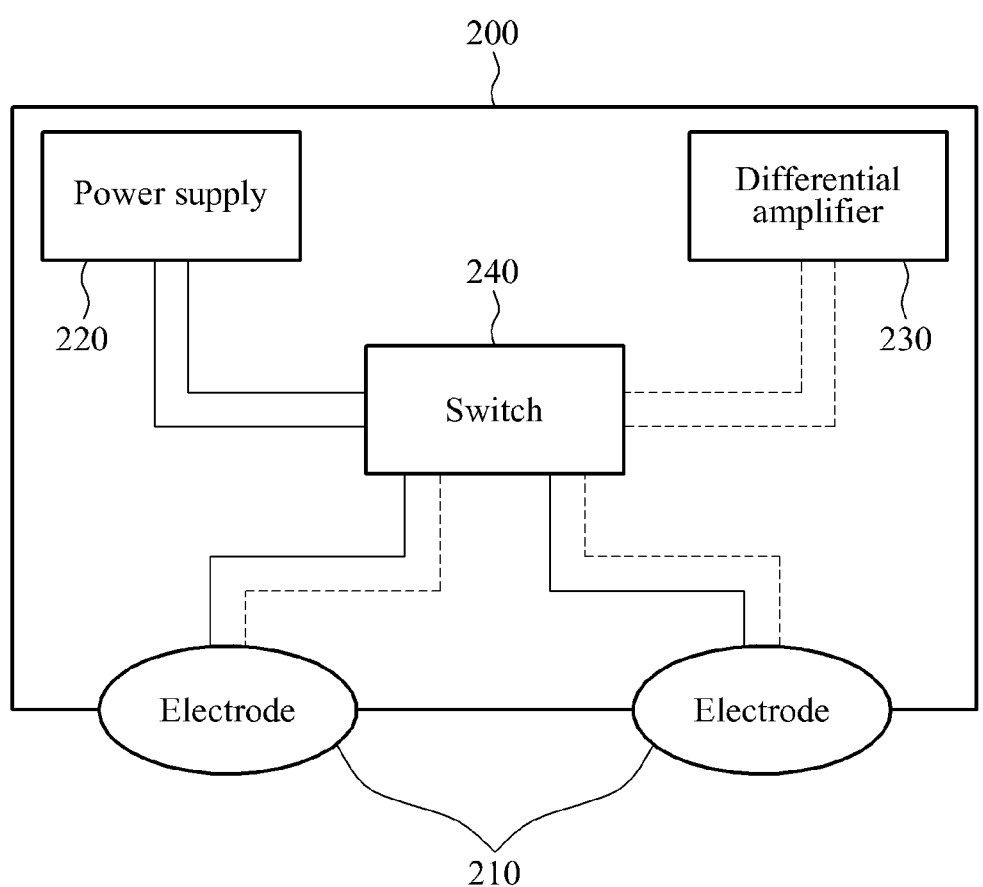
FIG. 2 is a diagram illustrating an example of a detailed configuration of an electrical stimulation device.

FIG. 2 illustrates an example of a detailed configuration of an electrical stimulation device 200.

The electrical stimulation device 200 includes an electrode 210, a power supply 220, and a differential amplifier 230. The electrical stimulation device 200 may further include a switch 240.

In this example, the electrode 210 is at least one electrode that is attached to a stimulation position. The electrode 210 outputs a stimulus signal to stimulate the stimulation position or a muscle of the stimulation position by outputting the stimulus signal. The electrode 210 performs detecting of an EMG signal occurring at the stimulation position or a muscle of the stimulation position.

For example, the electrode may measure an electrical signal such as a neural current extracted from the EMG signal. A shape of the electrode 210 may differ based on the location of the stimulation position. For example, FIG. 2 illustrates the electrode 210 having the shape of a circular patch, based on an inflectional body surface of the stimulation position.

In an example, the power supply 220 is an oscillation device that generates a stimulus signal, such as an alternating current (AC) power, based on a pattern input from the terminal device 110. The pattern is input through a communication network from the terminal device. For example, the power supply 220 generates a stimulus signal and output the stimulus signal to a stimulation position that is in contact with the electrode 210 based on the pattern.

The differential amplifier 230 measures an EMG signal at the stimulation position detected by the electrode 210. For example, the differential amplifier 230 outputs an output signal proportional to a difference of a plurality of input EMG signals and calculates a distribution value of the EMG signal.

The power supply 220 and the differential amplifier 230 may be selectively connected to or disconnected from the electrode 210. This may be based on an operation mode of the electrical stimulation device 200. The electrical stimulation device 200 may support the selective connection of the electrode 210, the power supply 220, or the differential amplifier 230 by further including the switch 240.

For example, when the electrical stimulus device 200 is operated in a mode for verifying whether the electrode 210 is attached to a predetermined stimulation position, the switch 240 connects the electrode 210 to the differential amplifier 230 and allows the EMG signal detected in the electrode 210 to be input to the differential amplifier 230.

When the electrical stimulus device 200 is operated in a mode for outputting the stimulus signal to the stimulation position, the switch 240 allows the stimulus signal generated in the power supply 220 to be outputted by disconnecting the connection between the electrode 210 and the differential amplifier 230 and connecting the electrode 210 to the power supply 220.

Figure 3:
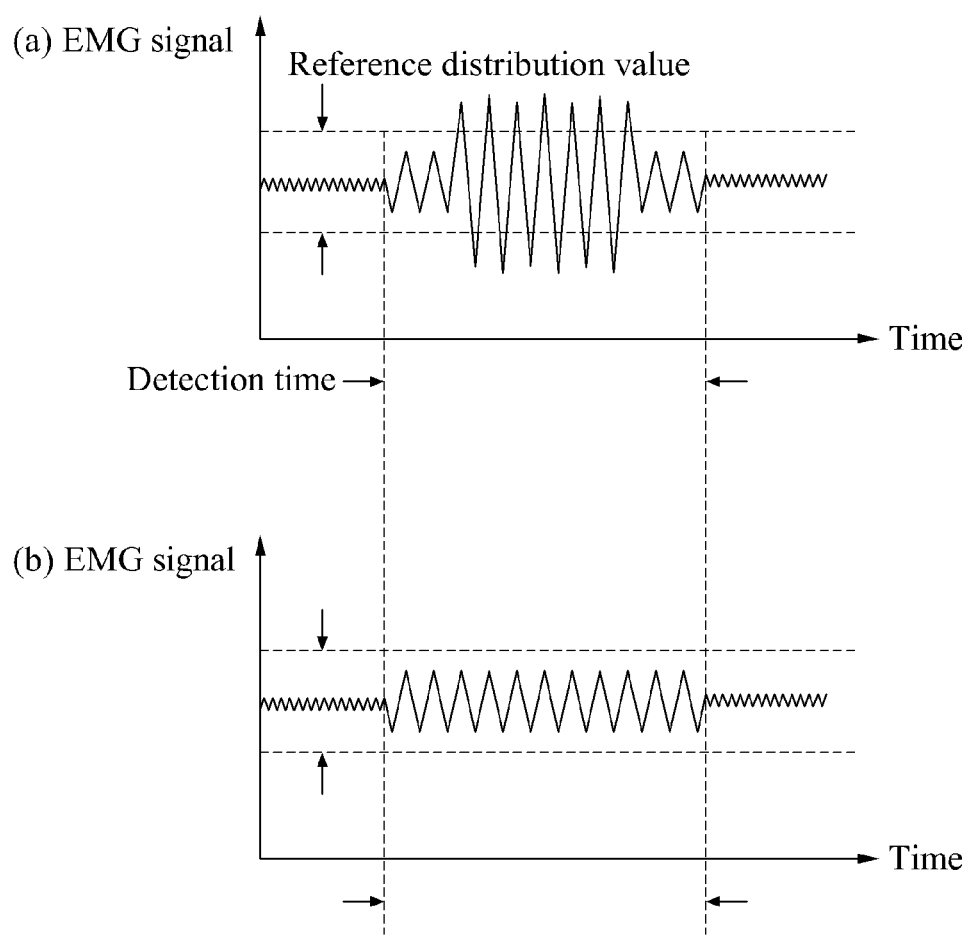
FIG. 3 is a diagram illustrating an example of a process of verifying that a position at which an electrode is attached is a predetermined stimulation position in an electrical stimulation device.

FIG. 3 illustrates an example of a process of verifying whether a position at which an electrode 210 is attached is the predetermined stimulation position in an electrical stimulation device 200.

Referring to FIGS. 2 and 3, the electrical stimulation device 200 detects an EMG signal at a portion at which the electrode 210 is currently attached to verify whether this positions corresponds to the predetermined stimulation position. In this example, the electrical stimulation device 200 determines whether the detected EMG signal satisfies a tolerance, and based on a result of the determination, determines whether to output the stimulus signal.

In detecting the EMG signal, the electrical stimulation device 200 detects a plurality of EMG signals from a plurality of electrodes 210 when the muscle is in a contracted state. The detecting of EMG signals is performed when the muscle is in a contracted state because a maximum value of EMG signals is detected and the electrical stimulation device 200 determines a position more precisely. The EMG signals are calculated as a distribution value by being input to the differential amplifier 230.

The electrical stimulation device 200 determines that the EMG signal satisfies the tolerance when the distribution of the EMG signal is greater than or equal to a predetermined reference distribution value. For example, graph (a) of FIG. 3 illustrates an example where the electrical stimulation device 200 determines that the location that the electrode 210 is currently attached corresponds to the predetermined stimulation position because the distribution of the EMG signal greater than or equal to the reference distribution value.

The electrical stimulation device 200 determines that the EMG signal fails to satisfy the tolerance when the distribution of the EMG signal is less than the reference distribution value. For example, graph (b) of FIG. 3 illustrates an example in which the electrical stimulation device 200 determines that the location that the electrode 210 is currently attached to is an inappropriate location because the distribution of the EMG signal is calculated to be less than the reference distribution value.

In this example, the electrical stimulation device 200 outputs information for adjusting the location of the electrode 210 when the EMG signal fails to satisfy the tolerance. This information may include a positioning information message, a warning alarm, and the like, that is output from the electrical stimulation device 200. The information for adjusting may be outputted as text, voice message, and the like, and induce a user to move the location of the electrode 210.

The electrical stimulation device 200 maximizes a stimulating effect to the muscle by verifying that the electrode 210 is disposed precisely at the predetermined stimulation position and outputting a stimulus signal to the stimulation position via the electrode 210.

Figure 4A:
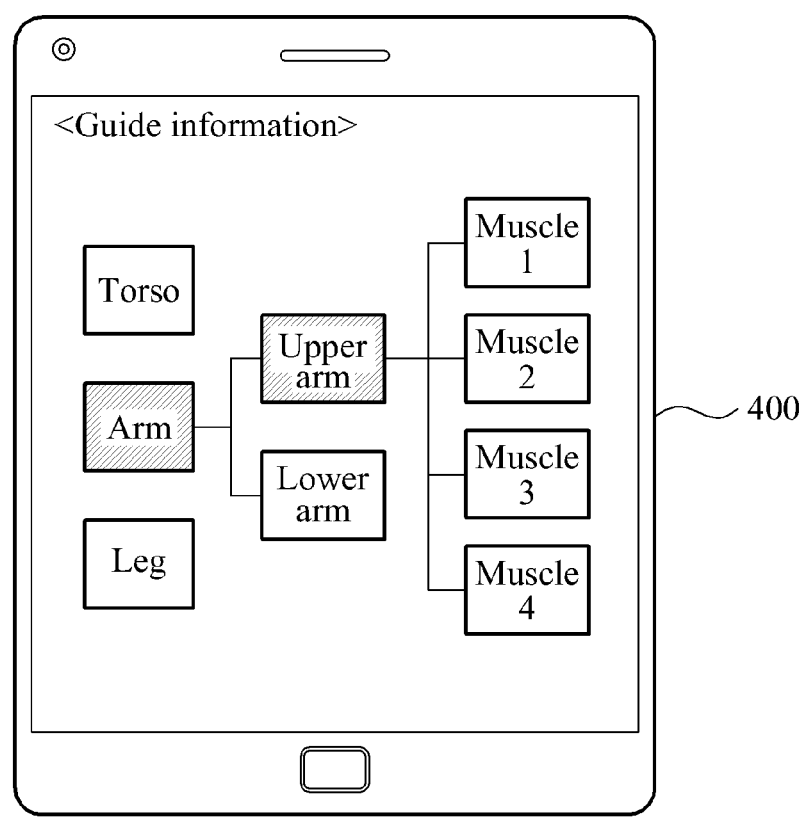
FIGS. 4A and 4B are diagrams illustrating examples of a terminal device for setting or predetermining a stimulation position.
Figure 4B:
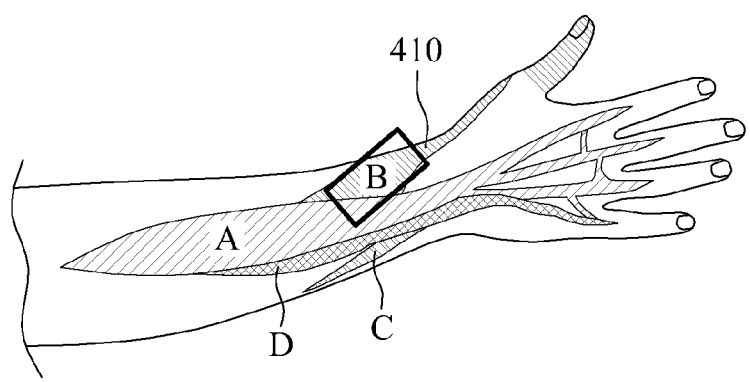

FIGS. 4A and 4B illustrate examples of a terminal device 400 for setting or predetermining a stimulation position.

The terminal device 400 may be implemented as a mobile terminal such as a smart phone, and the like. In this example, the terminal device 400 outputs guide information for attaching an electrode 122 to the stimulation position in response to an input from a user. For example, the terminal device 400 outputs guide information for attaching the electrode 122 to a stimulation position corresponding to an identified muscle in response to a particular input from the user.

Referring to FIG. 4A, the terminal device 400 provides guide information including a hierarchically classified menu according to a muscle input selected be the stimulation position. For example, the terminal device 400 provides a menu selection of "torso/arm/leg" in a main item field. In an example, when "arm" is selected by the user, a menu of "upper arm/lower arm" is provided in a sub-item field. Additionally, the terminal device 400 provides a menu selection of "muscle 1 through muscle 4" in a sub-item field with respect to the "upper arm" selected by the user. As a result, "muscle 2" in FIG. 4A may be selected by the user or may automatically be selected by the terminal device 400 based on a health condition, a state, or other circumstance of the user.

In this example, the terminal device 400 provides graphical or image information with respect to the predetermined stimulation position as guide information. For example, the terminal device 400 provides a position of the predetermined stimulation position "muscle 2" as a drawing. In FIG. 4B, an anatomical rendering of the "upper arm" to which the "muscle 2" belongs is illustrated, and a position 410 of the "muscle 2" is visually identified in the anatomical rendering. The terminal device 400 further provides text information reading "A stimulation position is a location to be identified by lifting of a thumb." This allows the position 410 of the "muscle 2" to be perceived and better identified by the user.

In another example, the terminal device 400 outputs guide information representing the stimulation position by a graphic or image where "muscle 2" has corresponding candidate locations A, B, C, and D at which the electrode 122 may be attached. In this example, the graphic or image of the terminal device 400 promotes location B as the location from which a maximum stimulation effect may be expected.

In an example, the terminal device 400 adjusts the environment under which the electrode 122 outputs a stimulus signal to the stimulation position to be an optimal environment. In this example, the terminal device 400 directs the electrode 122 to the location at which the electrode 122 is to be attached, based on a size, a weight, a flexibility, or other features of the electrical stimulation device 120 or the electrode 122.

In an example, the terminal device 400 generates a pattern that stimulates the optimal predetermined stimulation position. For example, the terminal device 400 provides a pattern of the stimulus signal for contracting and relaxing the muscle at the stimulation position. The terminal device 400 supports a user in programming a stimulation pattern directly. For example, the terminal device 400 outputs guide information for attaching the electrode 122 to the stimulation position and supports the user to edit the pattern of stimulation based on the guide information.

For example, the terminal device 400 supports the user to readily select or predetermine a location and a muscle to be stimulated by a simple selection from the user. The device 400 generates the stimulus signal in a manner preferred by the user by supporting an active editing with respect to the pattern.

Hereinafter, a process of operating the system 100 for skeletal muscle stimulation according to an example will be described in detail.

Figure 5:
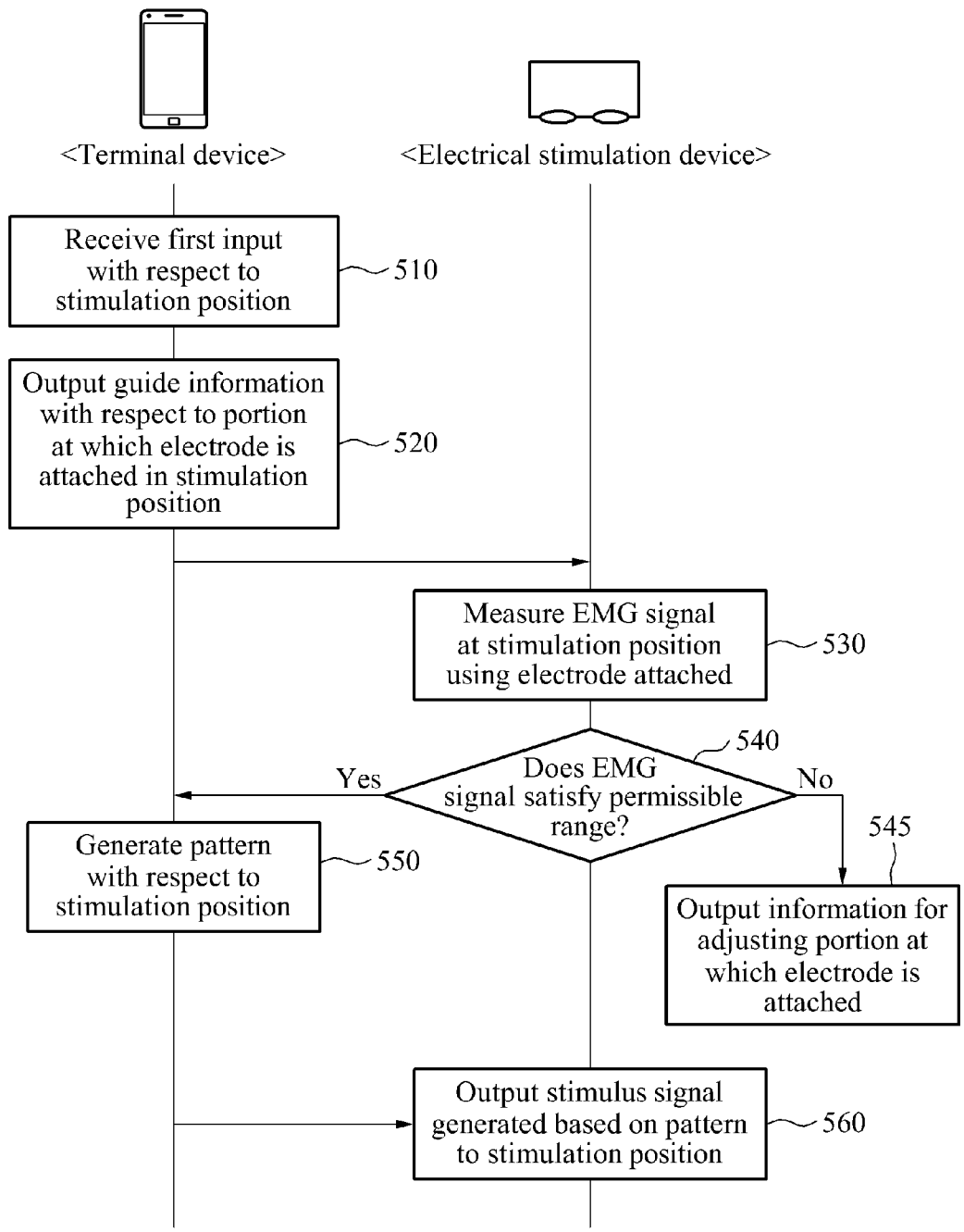
FIG. 5 is a flowchart illustrating an example of a method for operating a system for skeletal muscle stimulation.

FIG. 5 illustrates an example of a method for operating a system for skeletal muscle stimulation.

In this example, a scheme for implementing the system 100 for the skeletal muscle stimulation is conducted by an interactive operation of the terminal device 100 and the electrical stimulation device 120.

In 510, the terminal device 110 receives a first input from a user with respect to a stimulation position to be stimulated in a body. Operation 510 is a process in which a selection of a portion to be stimulated in the body is input from the user through an interface provided on the terminal device 110 such as a keypad, a touch pad, and the like.

In 520, the terminal device 110 outputs guide information representing the portion at which the electrode 122 is to be attached in response to the first input. Operation 520 is a process of outputting guide information and selecting or predetermining the stimulation position. The guide information includes a hierarchically classified menu that allows a user to select the stimulation position with ease.

In 520, when the stimulation position is predetermined, the terminal device 110 provides information corresponding to the position. For example, this information may include a location of the stimulation position, a shape of the associated muscle, usage of the muscle, and the like. For example, the terminal device 110 enables the user to perceive the corresponding stimulation position with ease by visually displaying information with respect to the stimulation position.

In 530, the electrical stimulation device 120 measures an EMG signal at the stimulation position using the attached electrode 122. Operation 530 is a process for determining a precise position of the stimulation position by detecting the EMG signal occurring in the body of the user via the electrode 122 attached to the electrical stimulation device 120.

In 540, the electrical stimulation device 120 determines whether the detected EMG signal satisfies a tolerance. Operation 540 is a process in which a location at which the electrode 120 is in contact with the user's body is determined to actually coincide or not conincide with the predetermined stimulation position.

In 540, the electrical stimulation device 120 determines that the EMG signal satisfies the tolerance by comparing a distribution of the EMG signal with a predetermined reference distribution. For example, when a muscle is in a contracted state, the electrical stimulation device 120 determines that the EMG signal satisfies the tolerance and determine that the electrode 122 is disposed precisely at the predetermined stimulation position (in a YES direction of the 540) when the distribution of the EMG signal is greater than or equal to the predetermined reference distribution value.

Alternatively, the electrical stimulation device 120 determines that the EMG signal fails to satisfy the tolerance and that the location of the electrode 122 differs from the predetermined stimulation position (in a NO direction of the 540) when the distribution of the EMG signal is less than the predetermined reference distribution value.

In 545, when the EMG signal fails to satisfy the tolerance (in the NO direction of the 540), the electrical stimulation device 120 outputs information for adjusting the location of the electrode 122. Operation 545 is a process of outputting a message or warning such as a positioning information message, a warning alarm, and the like, that directs the user to move the location of the electrode 122. The electrical stimulation device 120 may re-perform measuring of the EMG signal to verify a position by returning to operation 530 after the electrode 122 is moved.

If the EMG signal satisfies the tolerance (in the YES direction of 540), the terminal device 110 generates a pattern with respect to the stimulation position in 550. Operation 550 is a process of generating a pattern that stimulates the predetermined stimulation position and wirelessly transmitting the pattern to the electrical stimulation device 120 through a communication network. In this example, the pattern is a type of a program for strengthening a muscle by repetitive relaxation and contraction of the muscle. A period in applying a stimulus signal to the muscle may be adjusted according to the pattern.

In operation 550, the terminal device 110 receives a second input from the user with respect to the stimulation pattern and provides information about the pattern of the stimulus signal edited by the user in response to the second input. The terminal device 110 supports the user to perform direct programming and generate a pattern within a range of being medically safe for the user's body.

In 560, the electrical stimulation device 120 outputs the stimulus signal generated based on the pattern. Operation 560 is a process of generating the stimulus signal based on the pattern and outputting the stimulus signal to the stimulation position via the electrode 122 as the pattern is input from the terminal device 110. The terminal device and 110 and electrical stimulation device 120 may communicate wirelessly through a communication network.

According to various examples, there is provided a system 100 for skeletal muscle stimulation that enables a user to dispose an electrode 122 at a precise predetermined stimulation position. A user does not need to be familiar with anatomical terminology because the system 100 may provide comprehensive guide information in the terminal device 110 for illustrating the stimulation position by measuring an EMG signal in the electrical stimulation device 120.

According to various examples, it is possible to prevent muscle-aging of the elderly without physical exercise by outputting a stimulus signal based on a pattern generated for stimulating a muscle at a predetermined or preselected stimulation position.

The terminal device 110, electrical stimulation device 120, and all unit described above may be implemented using one or more hardware components, or a combination of one or more hardware components and one or more software components. A hardware component may be, for example, a physical device that physically performs one or more operations, but is not limited thereto. Examples of hardware components include controllers, microphones, amplifiers, low-pass filters, high-pass filters, band-pass filters, analog-to-digital converters, digital-to-analog converters, and processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

Software or instructions for controlling a processing device, such as those described in FIG. 5, to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code to that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for muscle stimulation, the apparatus comprising:
   an electrical stimulation device, comprising an electrode in contact with a muscle, and configured to
   wirelessly receive position information from a terminal device,
   use the electrode to measure an electromyogram (EMG) signal at a stimulation position; and
   determine whether the EMG signal is within a tolerance or outside of the tolerance,
   wherein, in response to the EMG signal being determined to be outside the tolerance, in response to a distribution of the EMG signal being greater than or equal to a reference distribution value for a muscle in a contracted state, the electrical stimulation device is configured to output information to the terminal device to adjust the position at which the electrode is in contact with the muscle, and
   wherein, in response to the EMG signal being determined to be within the tolerance, in response to a distribution of the EMG signal being less than the reference distribution value for the muscle in the contracted state, the electrical stimulation device is configured to communicate with the terminal device to receive a pattern from the terminal device with respect to the stimulation position, and output a stimulus signal to the stimulation position, based on the pattern.

2. The apparatus of claim 1, wherein the electrical stimulation device is further configured to output the stimulus signal, in response to the EMG signal.

3. The apparatus of claim 1, wherein the electrical stimulation device is wireless.

4. The apparatus of claim 1, wherein the electrical stimulation device comprises:
   a power supply configured to generate the stimulus signal; and
   a differential amplifier configured to measure the EMG signal.

5. The apparatus of claim 1, wherein in response to the electrical stimulation device outputting information to the terminal device to adjust the position at which the electrode is in contact with the muscle, the terminal device outputs guide information to a user, that enables the user to attach the electrode to the stimulation position.

6. The apparatus of claim 5, wherein the guide information comprises an image or an illustration.

7. The apparatus of claim 5, wherein the guide information corresponds to a muscle that is identified in response to the input from the user.

8. The apparatus of claim 7, wherein the terminal device is configured to provide a pattern of applying the stimulus signal for contracting or relaxing the muscle.

* * * * *